United States Patent
Baumann et al.

Patent Number: 5,624,551
Date of Patent: Apr. 29, 1997

[54] HYDRAULIC SAFETY CIRCUIT FOR A HEMODIALYSIS APPARATUS

[75] Inventors: Manfred Baumann, Schweinfurt; Helmuth Ender, Zeil, both of Germany

[73] Assignee: Fresenius AG, Bad Homburg, Germany

[21] Appl. No.: 233,294

[22] Filed: Apr. 26, 1994

[30]    Foreign Application Priority Data

Apr. 28, 1993 [DE] Germany ............................ 43 13 863.2
Jun. 24, 1993 [DE] Germany ............................ 43 21 008.2

[51] Int. Cl.$^6$ ............... B01D 36/00; G01M 3/26; G01M 3/28
[52] U.S. Cl. ................ 210/134; 73/40; 73/49.1; 137/456; 210/90; 210/96.2; 210/97; 210/136; 210/137; 210/252; 210/254; 210/258
[58] Field of Search ................ 210/252, 254, 210/258, 90, 96.2, 134, 136, 137, 321.69, 97, 929; 73/40, 40.5 R, 49.1; 137/456, 560, 563, 565

[56]    References Cited

U.S. PATENT DOCUMENTS

| | | | |
|---|---|---|---|
| 3,577,768 | 5/1971 | April, Jr. et al. | 73/40.5 R |
| 3,958,449 | 5/1976 | Drescher et al. | 73/40.5 R |
| 4,103,537 | 8/1978 | Victor | 73/40.5 R |
| 4,267,040 | 5/1981 | Schäl | 210/104 |
| 4,267,041 | 5/1981 | Schael | 210/109 |
| 4,355,654 | 10/1982 | Levesque et al. | 73/40.5 R |
| 4,530,759 | 7/1985 | Schäl | 210/104 |
| 4,770,769 | 9/1988 | Schael | 210/104 |
| 4,984,448 | 1/1991 | Jordan et al. | 73/40.5 R |
| 5,152,167 | 10/1992 | Moody | 73/40.5 R |

FOREIGN PATENT DOCUMENTS

| | | |
|---|---|---|
| 0052008 | 5/1982 | European Pat. Off. |
| 1927615 | 12/1970 | Germany. |
| 2838414 | 3/1980 | Germany. |
| 3923078 | 9/1990 | Germany. |
| 3907490 | 9/1990 | Germany. |
| 2045446 | 10/1980 | United Kingdom. |

Primary Examiner—John Kim
Attorney, Agent, or Firm—W. G. Fasse; W. F. Fasse

[57]    ABSTRACT

A hemodialysis apparatus is supplied with dialysis fluid or a dialysis fluid component through a supply loop conduit 12. A shut-off device 22, such as a magnetic valve, is arranged between the apparatus and the supply conduit 12. A buffer volume is enclosed between the shut-off device and an additionally arranged shut-off device such as a non-return valve. During disinfection of the apparatus, in order to prevent disinfecting fluid from flowing back into the supply loop conduit and therewith an endangering other dialysis apparatus connected to the same supply loop conduit, in the event that the shut-off device 22 leaks, the buffer volume is pressurized to a defined pressure, which is preferably higher than the pressure in the surrounding conduit sections. This pressure is detected by a pressure sensor P. The signal generated by the pressure sensor P is monitored by a microprocessor 28. Preferably, the pressure necessary in the buffer volume is generated by a pump 36, which is already present in state of the art dialysis apparatus. In this context, the invention also provides for a suitable switching valve arrangement.

22 Claims, 1 Drawing Sheet

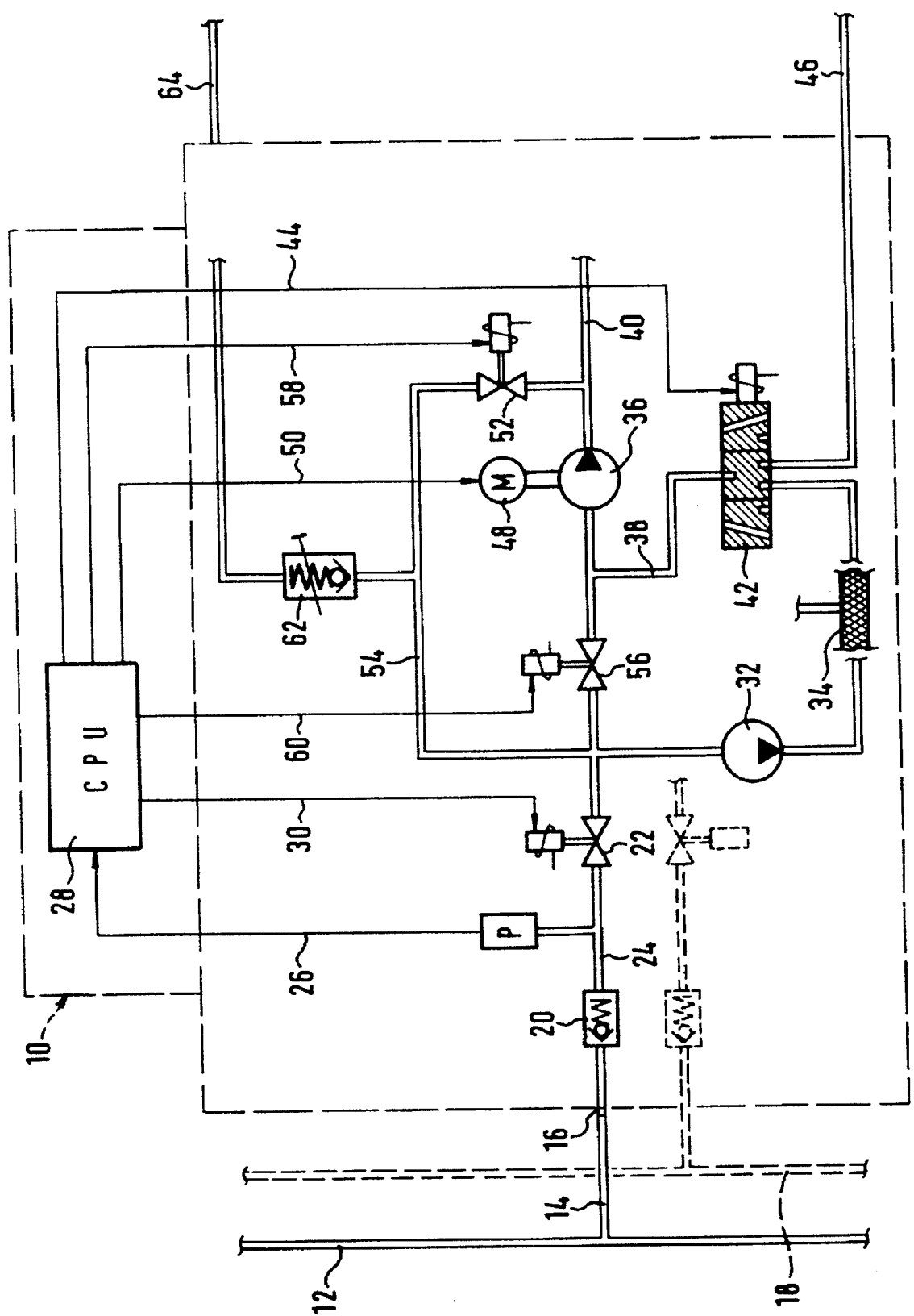

HYDRAULIC SAFETY CIRCUIT FOR A HEMODIALYSIS APPARATUS

FIELD OF THE INVENTION

The invention relates to a hydraulic safety circuit for a hemodialysis apparatus having the further features of the preamble of claim 1.

BACKGROUND INFORMATION

During the past decades, hemodialysis apparatus have achieved a high level of development and are used routinely in the treatment of patients with kidney diseases. The principle construction of a hemodialysis apparatus is known from German Patent No. 2.838.414.

In the case of hemodialysis apparatus that are designed as single-place or single-station units and are set up in a kidney patient's house, the dialysis fluid is sucked from canisters or merely a dialysis solution concentrate is sucked from a canister and then is mixed with water in the dialysis apparatus in order to produce the dialysis solution required for use in the machine. On the other hand, in hospitals with multiple dialysis stations or places, it has become the state of the art to connect each dialysis device by means of a connector to a supply conduit, embodied as a loop conduit. Such an arrangement or construction of a multi-station apparatus for the simultaneous treatment of multiple patients is known from European Patent Application No. 0.052.008.

In such a manner, the supply loop conduit can either supply a completely prepared dialysis fluid to the individual hemodialysis apparatus, or can merely supply individual components of the dialysis fluid, which is to be mixed in the dialysis apparatus, such as acid and bicarbonate for example. Especially in the latter case, it can also be that several supply- or ring-conduits are provided which deliver separate components, whereby an appropriate number of branch conduits flow from each ring conduit to each individual dialysis apparatus.

The supply conduit is usually connected to the dialysis apparatus by means of a connector, for example in the form of a coupling or the like. In this context, at least a (first) shut-off device is provided in the conduit portion from the supply conduit to the individual components of the dialysis apparatus, in order to prevent a backflow of fluid into the supply conduit. It is especially important to prevent such a backflow when the hemodialysis apparatus and the entire conduit system contained therein is being rinsed or flushed out with a cleaning and/or disinfecting solution, which is usually carried out after every treatment. If it enters the supply conduit, the comparatively strong or aggressive cleaning and disinfecting fluid can be carried to other dialysis apparatus connected to the conduit, thereby possibly resulting in a life-threatening situation if a dialysis treatment is being carried out on the other apparatus at the time.

While a backflow of fluid out of the conduit system of a dialysis apparatus into the supply conduit could be prevented by means of a simple non-return valve, it is furthermore desirable that no dialysis fluid flows out of the supply conduit into the conduit system of the dialysis apparatus during the cleaning of the dialysis apparatus, because a mixing of dialysis fluid and cleaning fluid can lead to reactions, which could damage the dialysis apparatus.

In order to solve this problem, it has been customary in dialysis apparatus according to the current state of the art, to install a magnetically controlled valve instead of a simple non-return valve in the conduit portion between the supply loop conduit and the dialysis apparatus.

In such an arrangement, the magnetic valve closes or blocks the conduit portion between the loop conduit and the dialysis apparatus in both directions and thus prevents a flow of fluid. However, because a backflow of disinfecting fluid into the supply conduit would be hazardous to people's lives, and thus by all means must be prevented, it is necessary to immediately detect any failure of the magnetic valve closing off the conduit. For safety reasons, therefore, the dialysis apparatus is separated from the loop conduit during the disinfection so as to be able to immediately detect any potentially occurring leakage of the magnetic valve and to reliably prevent a backflow of disinfecting fluid into the supply loop conduit carrying dialysis fluid.

Separating the hemodialysis apparatus from the supply conduit is, however, time consuming, expensive and moreover inconvenient for the hospital staff. Thus, on the one hand, costly losses of time can occur because the useful operating time of the hemodialysis apparatus is reduced, and on the other hand, the hospital staff may be tempted to dispense with separating the dialysis apparatus from the supply conduit in reliance upon the proper functioning of the magnetic shut-off valve, whereby the intended high safety standard is reduced.

SUMMARY OF THE INVENTION

In view of the above, it is the object of the invention to provide a safety circuit for a hemodialysis apparatus to be connected by means of a connector to a supply conduit, which makes possible a very high safety standard, and with which it is superfluous to separate the dialysis apparatus from the supply conduit during disinfection.

The inventive solution for achieving the above object in a hemodialysis apparatus according to the claim preamble is characterized by a hydraulic safety circuit having a second shut-off device arranged between the connector and the first shut-off device, so that a buffer volume is formed between the second and the first shut-off devices. The apparatus is further characterized by means for pressurizing the buffer volume to a defined pressure, a pressure sensor connected with the buffer volume, and an evaluation unit for a signal generated by the pressure sensor.

According to the invention, it is thereby preferably provided that the first shut-off device is a magnetic valve. Similarly, the second shut-off device can be a magnetic valve.

It is preferably provided, that the second shut-off device is a non-return valve and the defined pressure enclosed in the buffer volume is higher than the pressure prevailing in the supply conduit as well as higher than the flushing pressure prevailing on the apparatus-side of the shut-off device.

Such a hydraulic safety circuit enables monitoring the proper operation of the shut-off device in a simple manner. In one embodiment of the hydraulic safety circuit according to the invention, in which both the first and the second shut-off devices are embodied in the form of electrically controlled magnetic valves, the defined pressure enclosed in the buffer volume between the two magnetic valves can have any desired value, as long as this pressure differs from the pressure prevailing in the hemodialysis apparatus and in the supply loop conduit.

However, it is especially advantageous if the pressure selected for pressurizing the buffer volume is higher than the flushing pressure prevailing on the apparatus-side of the shut-off device and also higher than the pressure prevailing in the supply conduit. In such an embodiment, a non-return valve can be provided in place of the second magnetic valve, so that the buffer volume is enclosed between the non-return valve and the first shut-off device, which is preferably moreover in the form of a magnetic valve.

In such an embodiment, a drop in the pressure of the buffer volume is directly synonymous with a leak in either the shut-off device in the form of a magnetic valve or the non-return valve. The electric signal generated by the pressure sensor is preferably processed by a microprocessor, whereby a drop in the pressure can be quickly recognized and a signal can be emitted by the microprocessor, which can initiate any of a broad variety of possible measures.

In addition to the preferred embodiment described above, it is also contemplated that the defined pressure prevailing in the enclosed buffer volume—insofar as the buffer volume is formed between two magnetic valves—is either lower than the flushing pressure prevailing on the apparatus-side of the shut-off device, or lower than the pressure prevailing in the supply conduit or lower than both pressures. In such an embodiment, any deviation in pressure from the defined pressure value is interpreted as a fault condition, and a microprocessor, for example, can initiate the appropriate response measures. However, in such an embodiment, an unrecognizable fault condition can occur in rare cases, for example if a leak occurs in both the first and the second shut-off devices with both leaks having the same flow resistance. This situation is avoided in the preferred embodiment of the invention, wherein the pressure enclosed within the buffer volume is higher than both the pressure prevailing in the supply conduit and the flushing pressure prevailing on the apparatus-side of the first shut-off device.

In this manner, a secure or safe possibility is provided to detect and correspondingly react to a failure of the shut-off device in a short time, wherefore it is not necessary to separate the dialysis apparatus from the supply loop conduit during the disinfecting and cleaning process.

Various arrangements are possible as concrete embodiments of the pressure detector. In one embodiment, the pressure detector comprises a pressure-dependent switch that is switchable back and forth between two different switching states due to pressure, thus allowing the detector to register a drop in pressure below a defined limit pressure value. The primary advantage of such an embodiment is a low production cost.

While the means for pressurizing the buffer volume arranged between the non-return valve and the shut-off device can be embodied in any desired form, a pump is preferably used. Furthermore, it is preferable to use one of the pumps already present in the dialysis apparatus according to the state of the art, as the pump for developing the pressure. Such a pump can be a membrane pump, for example, which is provided for conveying dialysis fluid, or preferably a degassing pump embodied as a gear pump, which conveys the dialysis fluid necessary for the treatment through a degassing section.

Preferably in that context, the pressure side of the pump is directly or indirectly connected via a magnetic valve to the apparatus-side connector of the shut-off device which encloses the buffer volume, i.e. the first magnetic valve. The former or first-mentioned magnetic valve will also be denoted as the "third" magnetic valve in the following, so as to differentiate it from the "first" magnetic valve arranged at the interface between the supply conduit and the dialysis apparatus, and from the "second" magnetic valve used, as the case may be, instead of the above-mentioned non-return valve.

By means of such an arrangement, the pressure developed by the degassing pump can be used to pressurize the buffer volume, whereby the necessity of installing a second pump is avoided.

Therewith, an additional pump or another pressure generating apparatus is not necessary.

Further according to the invention, a pressure limiting valve can be directly or indirectly connected with the apparatus-side connector of the first shut-off device which bounds the buffer volume, i.e., the first magnetic valve.

Furthermore, another magnetic valve, designated as the "fourth" magnetic valve in the following, can be provided, through which the suction or intake side of the degassing pump can be directly or indirectly connected with or separated from the apparatus-side connector of the first shut-off device which encloses the buffer volume, i.e., the first magnetic valve. The advantage of such an arrangement is that during an operating mode of the safety circuit or the entire dialysis apparatus, in which, for forming the buffer volume, osmotic fluid is pumped into the first section of the supply conduit up to the non-return valve or up to the "second" magnetic valve used instead of the non-return valve, the osmotic fluid can be sucked up again so that it does not mix with dialysis fluids in a following dialysis procedure.

As already mentioned, it is preferable that the safety circuit comprises a microprocessor that monitors and further processes the signal generated by the pressure sensor. The microprocessor can advantageously be connected with the motor of the pump or with a motor control, so that the motor can be shut off immediately in the event of a fault condition, whereby further delivery of the disinfecting fluid is prevented. The invention further provides that the microprocessor is electrically connected with the three disclosed (first, second, and third) magnetic valves and that commands for opening and closing the magnetic valves can be generated and processed. In this embodiment of the invention, an appropriate program stored in the microprocessor can automate the entire process necessary for the operation of the safety switch, including building up the buffer volume pressure.

In the just preceding variant, in which the microprocessor is connected with the motor control of the pressure generating pump, it can also be provided, for example, that the volume or quantity delivered at the beginning of the disinfecting procedure, i.e. during pressurization of the buffer volume, is monitored, for example by counting the pump shaft revolutions. In this manner, it can be assured that only a limited quantity of osmotic fluid is pumped into the buffer volume, even in the event that the second shut-off device or non-return valve is defective.

Alternatively, the microprocessor can also be used to monitor the phase of the pressure build-up in the buffer volume at the beginning of the flush program. In the unlikely event that the non-return valve is defective while the first shut-off valve is open, there would be no build-up of pressure in the buffer volume because the delivered osmotic fluid would be forced into the supply loop conduit. Thus, the pressure switch or pressure sensor does not provide a signal corresponding to a pressure build-up to the microprocessor. While failure of the non-return valve is one case in which the pressure sensor does not provide a pressure signal to the microprocessor, a second case can exist in which the pressure sensor itself is defective. Therefore, it can be provided according to the invention that in the starting phase of the flushing program, i.e. when a pressure is to be built-up in the buffer volume, a lack of the signal from the pressure sensor is first evaluated to be an indication of a defective pressure sensor. Thus, the microprocessor triggers a corresponding display or signal, upon which the pressure sensor can be exchanged as a first step. If, upon a renewed attempt to pressurize the buffer volume during the starting phase of the flush program, the pressure signal from the pressure sensor is still lacking, then it should be taken to mean that the non-return valve or, in a respective corresponding embodiment of the invention, the second magnetic valve, i.e. the second shut-off device, is defective.

In any event, if a corresponding pressure signal from the pressure sensor is absent or lacking during the pressurization of the buffer volume, the microprocessor closes the first shutoff device and interrupts the flush program.

Furthermore, the safety circuit of the present invention can be operated as a pressure reducer in case the supply pressure $P_V$ prevailing in the supply conduit is higher than a defined limit value. To achieve this, the first shut-off device (first magnetic valve) connected to the microprocessor can be intermittently driven or controlled so that the pressure being established in the buffer volume is equal to or smaller than the defined limit value. Adjusting or matching the supply pressure to a desired lower pressure $P_V$ existing in the dialysis fluid supply conduit to a desired lower pressure can also be used to affect or influence the discharge or delivery characteristics of the membrane pump arranged in the dialysis apparatus.

The preferred method of flushing the conduit system of a hemodialysis apparatus, according to the invention, with a cleaning- and/or disinfecting-fluid, while simultaneously monitoring the proper function of the shut-off device (first magnetic valve) of the supply conduit, will be described below with reference to the drawing.

BRIEF DESCRIPTION OF THE DRAWING

In the drawing, the single Figure shows a schematic of the essential hydraulic and electrical circuit elements of a hemodialysis apparatus according to the present invention, whereby components that are not shown, but that are necessary for the actual dialysis, for example membranes, balancing chambers, etc., are simply denoted by a hatched area for the sake of clarity of the drawing.

DETAILED DESCRIPTION OF PREFERRED EXAMPLE EMBODIMENTS

The dialysis unit 10 of the invention is connected to a supply loop conduit 12, from which a branch conduit 14 branches off and is connected to the dialysis apparatus 10 at a connector joint 16. As indicated by a second supply loop conduit 18 shown by a dashed line, the dialysis apparatus 10 can be coupled to several supply loop conduits in the above described manner, whereby for example, a first supply loop conduit 12 carries an acidic solution and a second supply loop conduit 18 carries a bicarbonate solution. Downstream of the branch conduit 14, a non-return valve 20 is connected on the apparatus-side beyond the connector joint 16, followed by a first magnetic valve 22. As already explained, it is also possible to provide a second magnetic valve instead of the non-return valve 20. A buffer volume 24, embodied in the form of a conduit section or a strong tube or hose capable of bearing loads, and having a volume of a few milliliters, is enclosed between the non-return valve 20 and the first magnetic valve 22. Connected to the buffer volume 24 is a pressure sensor P that detects the pressure in the buffer volume and correspondingly generates an electrical signal that is provided via a conductor line 26 to a microprocessor 28. The first magnetic valve 22 is similarly connected to the microprocessor by a conductor line 30. If a second magnetic valve is provided instead of the non-return valve 20, then the valve is similarly connected to the microprocessor by a conductor line. A membrane feed pump 32 is connected behind the first magnetic valve 22. The pump 32 pumps the fluid delivered through the supply loop conduit 12, be it dialysis fluid or a dialysis fluid component, into the conduit system 34, which is not shown in detail, but which is known in total in the current state of the art.

A second pump 36 is used as a so-called degassing pump and sucks dialysis fluid through a conduit 38 out of the conduit system 34 of the dialysis apparatus, which is not described in greater detail, and drives the fluid through a conduit 40 to a degassing section or station, which is not shown. In order to achieve this, in the exemplary embodiment of the hemodialysis apparatus according to the invention that is shown in the drawing, a 3/2-way valve 42 is switched into the appropriate position. The 3/2-way valve is also connected with the microprocessor 28 (CPU) by means of a conductor line 44.

In another switching position, the 3-way valve 42 connects the suction conduit 38 of the degassing pump 36 with a delivery conduit 46 for cleaning- and/or disinfecting fluid.

A motor 48 of the pump 36 is connected with the microprocessor 28 by means of a conductor line 50.

The pressure side of the degassing pump 36 is connected to the apparatus-side connector of the first magnetic valve 22 by means of a third magnetic valve 52 and a conduit 54.

In this example embodiment, a fourth magnetic valve 56 is connected in series with the first magnetic valve 22 and leads to the suction or intake side of the degassing pump 36. The first, third and fourth magnetic valves 22, 52 and 56 are connected via electrical lines 30, 58 and 60 to the microprocessor.

A high pressure relief valve 62 is connected to the conduit 54, which leads from the pressure side of the degassing pump 36 through the third magnetic valve 52 to the first magnetic valve 22. The relief valve 62 opens, for example, at a pressure of about 1.2 bar.

It is symbolically indicated, that the entire dialysis apparatus 10 is provided with a drain 64. Just as with the symbolic representation of the conduit system 34, this is intended to indicate that the complete hydraulic circuit construction of the hemodialysis apparatus of the invention is substantially more complex than shown here.

During normal operation, that is, during dialysis, the first magnetic valve 22 is switched open for through flow, the fourth magnetic valve 56 is closed, the three-way valve 42 is switched so that the suction conduit 38 of the degassing pump 36 is connected with the correspondingly provided, portion of the conduit system 34 which is not shown in detail, and the third magnetic valve 52 is similarly closed.

The dialysis fluid or one of its components passes from the supply loop conduit 12 and through the branch conduit 14 and the connector 16, through the non-return valve 20 into the conduit portion 24 forming the buffer volume. From there the fluid travels through the open first magnetic valve 22 to the suction side of the membrane feed pump 32. The membrane feed pump 32 pumps the dialysis fluid into the conduit system 34, 38 where the dialysis process, which is not described in further detail here, is carried out according to the state of the art. After the dialysis, the used dialysate leaves the dialysis apparatus through the drain conduit 64.

If the dialysis apparatus is to be disinfected and cleaned after the completed dialysis treatment, then the following process is automatically carried out upon corresponding activation by the microprocessor (CPU) 28:

First, the fourth magnetic valve 56 is kept closed as it was and the 3-way valve 42 is switched so that the suction side of the degassing pump 36 is connected with the conduit system 34 by means of the conduit 38. The third magnetic valve 52 is then opened, and osmotic fluid is sucked out of the conduit system 34 and forced via conduit 54 through the first magnetic valve 22 into the buffer volume 24 up to the non-return valve 20.

During this phase of pressurizing the buffer volume 24, the signal 26 provided by pressure sensor P is monitored by the microprocessor 28. If a pressure increase is not registered, it is first assumed that the pressure sensor P is defective and the flushing program is interrupted. A corresponding error message is issued or released, so as to indicate that the pressure sensor is to be exchanged.

After the pressure sensor is exchanged, the process of pressurizing by means of osmotic fluid pumped by the degassing pump 36 is repeated. If it again occurs that the signal from the pressure sensor P signalling a pressure increase is failing or lacking, then it is assumed this time that the non-return valve 20 is defective and once again the flushing program is interrupted.

In the case that a proper pressure increase is at hand, the degassing pump 36 pumps osmotic fluid through the open third magnet valve 52 until the high pressure relief valve 62 opens and any further delivered osmotic fluid flows out through the conduit connected thereto. Now the pressure sensor P signals to the microprocessor 28 that the defined pressure has been reached, whereupon the first shut-off device, that is the first magnetic valve 22, is closed. At this time, a defined pressure prevails in the buffer volume 24, wherein the defined pressure is higher than the supply pressure $P_V$ prevailing in the supply conduit 12 or the branch conduit 14 as well as higher than the flushing pressure $P_S$ which is used later for flushing the system. If this pressure $P_{PV}$ then decreases during the following disinfecting process, it can be assumed therefrom, that fluid is flowing out either through the first magnetic valve or through the non-return valve 20, which is synonymous with a leak or with a failure condition.

The 3-way valve 42 is toggled or switched for carrying out the actual flushing process. First, it is switched so that the suction side of the degassing pump 36 is connected with the disinfecting fluid suction conduit 46 by means of the conduit 38 and the 3-way valve 42. Disinfecting fluid is sucked up, and with the first shut-off device, i.e. the first magnetic valve, being shut, the fluid is delivered through the conduit 54 and the membrane pump 32 into the conduit system 34, which is to be disinfected. Then, the 3-way valve 42 closes again so that the suction side of the degassing pump 36 is connected by the conduit 38 to the conduit system 34. The membrane pump 32 conveys the disinfecting fluid through the conduit system 34, which is to be disinfected. The process can be repeated if necessary.

In the embodiment of the hemodialysis apparatus according to the invention shown here as an example, it is further possible to alternately close and open the third magnetic valve and the fourth magnetic valve in opposition. By cycling the two above named magnetic valves in this manner it is assured that the disinfecting fluid being circulated flushes through the conduit system 34 as well as the conduit 54, so that the entire hemodialysis apparatus is disinfected.

After the flushing process is completed, the microprocessor 28 can generate a signal that opens the fourth magnetic valve 56, similarly as the first shut-off device, i.e. the first magnetic valve 22. With the third magnetic valve 52 closed, the fluid contained in the buffer volume 24 can be sucked up, by the degassing pump 36 in the instant case at hand, before the hemodialysis apparatus is switched over to normal operation, in which dialysis fluid is conveyed out of the loop conduit 12, through the branch conduit 14, the non-return valve 20, the buffer volume 24 and the first magnetic valve 22 and flows through the conduit system 34.

During the entire flushing process, the signal generated by the pressure sensor P is monitored and thereby it is assured that the first shut-off device in the form of the first magnetic valve 22 is operating properly and a definite or strict separation between the supply conduit 12 and the hemodialysis apparatus is assured while disinfecting fluid is present in the apparatus. In this manner, the safety of the unit is clearly increased without it being necessary to completely disconnect the hemodialysis apparatus from the supply network in order to carry out the disinfecting process.

Although the invention has been described with reference to specific example embodiments, it will be appreciated that it is intended to cover all modifications and equivalents within the scope of the appended claims.

We claim:

1. In a hemodialysis apparatus having a conduit system including a first connector that is to be connected to a source of dialysis fluid, a second connector that is to be simultaneously connected to a source of flushing fluid, and a pressurizing pump selected from the group consisting of a membrane pump and a dialysis fluid degassing pump arranged in the conduit system, an improved hydraulic safety circuit arranged in the conduit system between the first connector and the second connector to avoid mixing of the dialysis fluid and the flushing fluid, said safety circuit comprising a first shut-off device arranged in the conduit system between the first connector and the second connector and having a buffer-side port arranged toward the first connector and an apparatus-side port arranged away from the first connector, a second shut-off device connected between the first connector and said buffer-side port of said first shut-off device, a sealable buffer volume that is formed between said first and second shut-off devices and that is sealed when said first and second shut-off devices are closed, the pressurizing pump being connected to said buffer volume for pressurizing said buffer volume to a defined pressure, a pressure sensor connected to said buffer volume, and an evaluating unit connected to a signal output of said pressure sensor to evaluate any deviation from said defined pressure in said buffer volume to detect any leakage through at least one of said first and second shut-off devices when said first and second shut-off devices are closed.

2. The hydraulic safety circuit of claim 1, wherein said first shut-off device comprises a first magnetic valve.

3. The hydraulic safety circuit of claim 2, wherein said second shut-off device comprises a non-return valve and wherein said defined pressure in said buffer volume is set to be greater than a supply pressure upstream of said non-return valve and greater than a flushing pressure on said apparatus-side port of said first shut-off device.

4. The hydraulic safety circuit of claim 1, wherein said second shut-off device comprises a magnetic valve.

5. The hydraulic safety circuit of claim 1, wherein said second shut-off device comprises a non-return valve and wherein said defined pressure in said buffer volume is set to be greater than a supply pressure upstream of said non-return valve and greater than a flushing pressure on said apparatus-side port of said first shut-off device.

6. The hydraulic safety circuit of claim 1, wherein said pressure sensor comprises an analog pressure sensor.

7. The hydraulic safety circuit of claim 1, wherein said pressure sensor comprises a pressure dependent switch.

8. The hydraulic safety circuit of claim 1, wherein the pressurizing pump is a membrane pump.

9. The hydraulic safety circuit of claim 1, the pressurizing pump is a dialysis fluid degassing pump.

10. The hydraulic safety circuit of claim 9, further comprising a magnetic valve, wherein a pressure outlet of said pressurizing pump is connected to said apparatus-side port of said first shut-off device through said magnetic valve.

11. The hydraulic safety circuit of claim 10, further comprising another magnetic valve, wherein a suction inlet of said pressurizing pump is connected to said apparatus-side port of said first shut-off device through said another magnetic valve.

12. The hydraulic safety circuit of claim 1, further comprising a magnetic valve, wherein a pressure outlet of said pressurizing pump is connected to said apparatus-side port of said first shut-off device through said magnetic valve.

13. The hydraulic safety circuit of claim 12, further comprising a pressure limiting valve connected to said apparatus-side port of said first shut-off device.

14. The hydraulic safety circuit of claim 13, wherein said pressure limiting valve has a trigger pressure value of about 1.2 bar.

15. The hydraulic safety circuit of claim 12, wherein said evaluating unit comprises a microprocessor, said pressurizing pump comprises a pump motor, and said pump motor is connected to said microprocessor.

16. The hydraulic safety circuit of claim 12, wherein said evaluating unit comprises a microprocessor and said magnetic valve is electrically connected to said microprocessor.

17. The hydraulic safety circuit of claim 1, further comprising a magnetic valve, wherein a suction inlet of said pressurizing pump is connected to said apparatus-side port of said first shut-off device through said magnetic valve.

18. The hydraulic safety circuit of claim 17, wherein said evaluating unit comprises a microprocessor and said magnetic valve is electrically connected to said microprocessor.

19. The hydraulic safety circuit of claim 1, wherein said evaluating unit comprises a microprocessor, said pressurizing pump comprises a pump motor, and said pump motor is connected to said microprocessor.

20. The hydraulic safety circuit of claim 19, wherein said evaluating unit comprises a microprocessor, wherein said first shut-off device comprises a first magnetic valve which is connected to said microprocessor, and wherein said pressure sensor, said first magnetic valve and said microprocessor together form a pressure reducer during normal dialyzing operation of the hemodialysis apparatus when a supply pressure of the dialysis fluid from the source of dialysis fluid is greater than a threshold value.

21. A hydraulic safety circuit for a hemodialysis apparatus that is to be connected to a source of dialysis fluid and to a source of flushing fluid, said safety circuit comprising a first connector adapted to be connected to the source of dialysis fluid, a second connector adapted to be connected to the source of flushing fluid, a first shut-off device arranged between said first connector and the hemodialysis apparatus and having an apparatus-side port arranged toward the hemodialysis apparatus and a buffer-side port arranged toward said first connector, a second shut-off device connected between said first connector and said buffer-side port of said first shut-off device, a sealable buffer volume formed between said first and second shut-off devices, means for pressurizing said buffer volume to a defined pressure, a pressure sensor connected to said buffer volume, an evaluating unit connected to a signal output of said pressure sensor to evaluate any deviation from said defined pressure in said buffer volume, and a fourth magnetic valve arranged between said apparatus-side port of said first shut-off device and an inlet of said means for pressurizing.

22. In a hemodialysis apparatus having a conduit system including a first connector that is to be connected to a source of dialysis fluid, a second connector that is to be simultaneously connected to a source of flushing fluid, and a pressurizing pump arranged in the conduit system,
an improved hydraulic safety circuit arranged in the conduit system between the first connector and the second connector to avoid mixing of the dialysis fluid and the flushing fluid, said safety circuit comprising a first shut-off device arranged in the conduit system between the first connector and the second connector and having a buffer-side port arranged toward the first connector and an apparatus-side port arranged away from the first connector, a second shut-off device connected between the first connector and said buffer-side port of said first shut-off device, a sealable buffer volume that is formed between said first and second shut-off devices and that is sealed when said first and second shut-off devices are closed, the pressurizing pump being connected to said buffer volume for pressurizing said buffer volume to a defined pressure, a pressure sensor connected to said buffer volume, an evaluating unit connected to a signal output of said pressure sensor no evaluate any deviation from said defined pressure in said buffer volume to detect any leakage through at least one of said first and second shut-off devices when said first and second shut-off devices are closed, and a magnetic valve arranged such that a pressure outlet of the pressurizing pump is connected to said apparatus-side port of said first shut-off device through said magnetic valve.

* * * * *

UNITED STATES PATENT AND TRADEMARK OFFICE
CERTIFICATE OF CORRECTION

PATENT NO.   : 5,624,551
DATED        : Apr. 29, 1997
INVENTOR(S)  : Baumann et al.

It is certified that error appears in the above-identified patent and that said Letters Patent is hereby corrected as shown below:

On the Title Page:
In [57] ABSTRACT, line 9, replace "therewith an" by --thereby--.

Column 9, line 7, after "claim 1," insert --wherein--.

Column 10, line 19, delete "fourth";
          line 45, replace "no" by --to--.

Signed and Sealed this

Twenty-ninth Day of July, 1997

Attest:

BRUCE LEHMAN

Attesting Officer

Commissioner of Patents and Trademarks